United States Patent [19]

Akers et al.

[11] 4,074,027

[45] Feb. 14, 1978

[54] GENERATING DEVICE UTILIZING IRRADIATED COPPER ELECTRODE

[76] Inventors: Raymond F. Akers, 202 Summit Ave., Mantua, N.J. 08051; Frank Malley, 112 Hughes Ave., Gloucester, N.J. 08030

[21] Appl. No.: 774,467

[22] Filed: Mar. 4, 1977

[51] Int. Cl.² .......................................... H01M 10/24
[52] U.S. Cl. ..................................... 429/10; 429/218; 429/220; 429/229; 29/623.1
[58] Field of Search .............................. 429/10, 90–93, 429/110, 118, 119, 220, 218, 249, 229; 204/195 R, 292, 293; 324/30 R, 30 B, 29.5, 30 A; 29/623.1

[56] References Cited

U.S. PATENT DOCUMENTS

| | | | |
|---|---|---|---|
| 86,221 | 1/1869 | Geiger | 429/220 |
| 324,475 | 8/1885 | Lyman | 429/220 |
| 1,332,483 | 3/1920 | Bridge | 429/119 |
| 2,794,904 | 6/1957 | Salanze | 429/118 X |
| 3,113,891 | 12/1963 | Comanor et al. | 429/220 X |
| 3,427,201 | 2/1969 | Burant et al. | 429/119 |

Primary Examiner—Anthony Skapars
Attorney, Agent, or Firm—Woodcock, Washburn, Kurtz & Mackiewicz

[57] ABSTRACT

A generating device is disclosed comprising first and second electrodes made of dissimilar metals, one of said electrodes being copper which has been irradiated with electromagnetic energy at the wavelength for excitation of the K shell electrons of the copper atoms. The other electrode contains at least one element chosen from Periodic groups I, II, III, IV, VII and VIII, and is preferably nickel plated brass. The two electrodes, when maintained in an electrolyte, provide a stable electrical output. When the ion concentration of the electrolyte is below a given level, the output is proportional to the ion concentration, such that an ion detector is provided.

23 Claims, 2 Drawing Figures

GENERATING DEVICE UTILIZING IRRADIATED COPPER ELECTRODE

BACKGROUND OF THE INVENTION

1. Field of the Invention

This invention lies in the area of ionic generating devices or cells and, more particularly, in the area of long lasting electrical energy cells capable of producing an electrical signal derived from the ion concentration of an electrolyte.

2. Description of the Prior Art

The prior art discloses a wide variety of cells and battery devices which represent a range of capabilities in terms of power output and lifetime. For example, sea water batteries have been disclosed and patented, which batteries utilize sea water as an electrolyte for generating power from the galvanic corrosion of the cathode material. A wide variety of galvanic type batteries are also found in the patent literature, as are deferred-action type cells which are adapted for activation by immersion in an activating liquid. However, as is well known, there always exists a need for improvement in this very important area, and particularly for improvement such as renders more uniform cell performance over a long period of time.

A specific area where there is a great need for the development of an improved ionic generating device is in the area of ion detectors. There is a substantial need in industry for improved instrumentation for detection of water purity. For example, it is necessary to obtain water which is pure within certain standards in order to reduce the corrosive characteristics caused by water containing certain ions when used in complex equipment. Additionally, many industrial and commercial chemical processes require water of a purity which is higher than that which is commercially available. Typical prior art devices used to measure the ion concentration of water or other aqueous solutions are conductivity type devices wherein two or more electrodes are placed in a test solution and an electrical potential is then placed across the electrodes. A bridge circuit or other sensing circuit is then utilized to determine the relative conductivity of the test solution, thereby giving a reading of the ion concentration. This type of approach is limited in terms of the lower range of sensitivity that is available, it being very difficult to measure ion concentrations below 1 part per million with this type of conductivity device. Some of the limitations of this type of instrumentation are well known, e.g., bubble formation around the electrodes which causes false changes in the conductivity; the temperature sensitivity of the conductivity measurement; corrosion of the electrodes; the effect of geometry such as the size of the electrodes and the space of the electrodes. In short, not only does the present ion detection instrumentation not provide the type of sensitivity that is required, but it appears as though the conductivity measurement type of device has inherent limitations such as will not permit the more accurate measurements which are required to detect trace concentrations of ions. There is thus a substantial need for a device which will operate on the principle of generating a signal as a function of ion concentration, which device will reliably and efficiently operate to provide measurements of extremely low ion concentrations.

SUMMARY OF THE INVENTION

It is an objective of this invention to provide a long life generating cell having improved performance characteristics.

It is another objective of this invention to provide an inexpensive and reliable device for providing electrical energy.

It is another object of this invention to provide an inexpensive and reliable cell for producing electrical energy, which cell provides a relatively constant output over a long period of time, and which can be easily adapted to have an internal impedance characteristic which can be varied within a predetermined range.

It is another objective of this invention to provide an inexpensive and relatively simple method of making an improved cell.

It is yet another objective of this invention to provide an improved cell which can be used in combination with an output device to provide an ion detector requiring no external source.

It is yet another object of this invention to provide the ion detector as described immediately above and which is capable of detecting trace amounts of ions.

It is another objective of this invention to provide an ion detector incorporating an inexpensive probe which comprises an ion powered cell.

It is a still further objective of this invention to provide an improved ion detector which incorporates an improved ion powdered cell which is long lasting and which is characterized by maintaining substantially constant characteristics over long periods of time and providing an instant reading of the ion content of the sampled electrolyte.

It is a still further objective of this invention to provide an ion detector which does not require batteries or any other energy source, and which incorporates an improved cell which is inexpensive and easy to manufacture, which detector is adapted to reliably and accurately detect trace amounts of ion concentrations in water, e.g., less than 15 parts per million.

In accordance with the above objectives, there is provided a unique generating device, or cell, comprising first and second electrodes made of dissimilar metals, one of said electrodes being copper which has been irradiated with electro-magnetic energy at a wavelength at or about 1.378 A, which is believed to be an energy which excites K shell electrons of the copper atoms. The other electrode contains at least one element chosen from periodic groups I, II, VI, VII, and VIII. The two electrodes are maintained in an electrolyte, for example an aqueous solution which contains a given ionic content. When ions are present in the electrolyte in trace amounts, e.g., around 1 PPM, the output is proportional to the ion concentration, and combination of the cell with means for reading current flow therefrom provides a reliable ion detector for detecting trace amounts of ions in solution. The sensitivity of the ion detector of this invention, when a 0-50 microamp meter is used, is at least as low as 0.5 PPM NaCl. The ion detector is capable of sensing even lower ion concentrations by the utilization of conventional low signal electronic circuitry.

DESCRIPTION OF THE PREFERRED EMBODIMENTS

Figure 1:
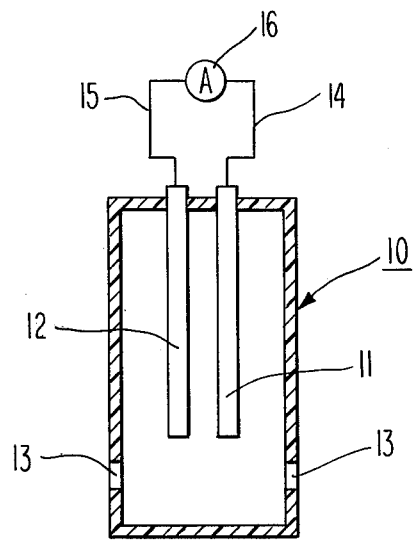
FIG. 1 is a schematic diagram of the basic simple configuration of the ion generating cell of this invention. The figure also illustrates a current reading meter connected to the electrodes of the cell, the cell and the meter together providing an ion detector.

Referring now to FIG. 1, there is illustrated schematically an ionic generating device which is housed in a chamber 10 made of a non-conductive material such as an organic polymer, suitably polyvinylchloride. Other materials, such as epoxy resins, are also effective. A pair of electrodes 11 and 12 respectively are provided, which electrodes are mounted such that they each have exposed surfaces within the interior of the housing 10. Housing 10 contains within it an electrolyte, which electrolyte contains a certain ion concentration. As used herein, the term electrolyte refers to a non-metallic and generally aqueous solution in which current is carried by the movement of free ions. For example, ordinary sea water, or water containing small amounts of dissolved NaCl, is such a suitable electrolyte. However, the invention is not limited to sea or salt water, but embraces any type of solution in which free ions are present.

Housing 10 may either be enclosed, in which case it presents a sealed and contained interior which holds the electrolyte, or it may contain openings 13 which permit the electrolyte to flow into and fill the interior. The latter embodiment is useful where, for example, the generating cell is to be used in conjunction with 16 as an ion detector. In this embodiment, the cell is physically in the form of a probe which is immersed into the water which is to be tested, the openings 13 permitting the water to flow into the interior of the cell so that ion generation can take place between electrodes 11 and 12. Leads 14 and 15 connect electrodes 11 and 12 respectively to the ammeter 16, providing a direct current readout which is proportional to the ion content of the electrolyte.

The electrode 11 is comprised of a first metal, preferably copper, which has been irradiated with high frequency electromagnetic radiation. In the case of copper, it has been found that irradiation of the copper electrode 11 provides maximum improvement to the performance of the resulting cell when centered around a wavelength of about 1.378 A. This wavelength is the equivalent of 8950 volts, and is believed to represent K shell excitation energy for copper atoms. The experiments have indicated that the improvement obtained in the performance of the cell of this invention depends upon the prior irradiation of the copper electrode, and such improvement peaks at this particular radiation wavelength. The electrode should be irradiated such that all portions thereof are exposed and receive the high frequency radiation.

Electrode 12 is suitably a nickel plated brass of standard composition, i.e., 15% zinc and 85% copper. The nickel plating may be applied by conventional methods. Electrode 12, referred to as the negative electrode, may be comprised of a metal or metallic compounds of elements of groups I, II, III, VI, VII and VIII of the Periodic Table. The metal, or compound or alloy thereof, must be stable when immersed in the electrolyte, and not be such that the electrolyte is corrosive to it. In particular, metals and mixtures of metals from groups I, II and VIII of the Periodic Table are preferred, and in turn it is more preferred that the negative electrode contain at least 2 metals chosen from said groups I, II and VIII. Electrode compositions which give satisfactory results for the device of this invention include brass, iron, stainless steel, aluminum, zinc, nickel, chrome plated brass, and other like metals and combinations. More particularly, it has been found that compositions containing zinc, nickel and copper are effective.

It has been found that the precise geometry of the component elements of the cell of this invention are not particularly critical in terms of affecting the electrical characteristics, but that the step of irradiating the copper electrode is in fact critical and important. The size and surface areas of the respective electrodes may vary considerably without significantly affecting the electrical characteristics. Likewise, the amount, i.e., volume of the electrolyte contained within housing 10 is a secondary variable, i.e., has only a minor effect. When used in combination with a meter such as a 0–50 $\mu a$ meter or other current sensing electronic circuitry, the cell electrodes 11 and 13 may be suitably 1 to 3 cm long and 5 to 10 mils in diameter. The distance between electrodes may range from less than 0.001 inch to about 5 inches with very little effect on the electrical characteristics, an interelectrode distance of about 3 inches being suitable for the ion detector application.

Tests of the cell shown in FIG. 1 have been run wherein a thimblefull of tap water has effectively fueled the ionic generating device for many months. The same electrodes, when placed in a liter of identical tap water fluid, produce the same output. It has been found that when the copper rod is pretreated by irradiation, the cell provides a very uniform and constant output over a long period of time. In fact, a cell in accordance with FIG. 1, where the electrolyte is salt water, has been under test for about 6 months, and has produced a constant output of about 350 $\mu a$ at about 1 volt, without any observable deterioration of this output characteristic. However, for the exact same cell, if the copper electrode is not first radiated, the output tapers off in a period of time within the range of about 5 minutes to 2 hours, and provides a drastically diminished output.

It has been found that for ion concentrations such as found in typical sea water, and below, the current output is substantially linearly proportional to the ion concentration, making the arrangement of FIG. 1 ideal for ion detection. When used as an ion detector, it has been found that the cell of FIG. 1 is sensitive to electrolytes having conductivity levels down to 1 micromho per centimeter, or 0.5 PPM NaCl. This sensitivity can be obtained simply with a standard meter having a range of 0 to 50 $\mu a$. By replacing the simple microammeter with more sophisticated but conventional electronic circuitry, capable of processing low signal to noise inputs, detection of ion concentrations well below 0.5 PPM, as in ultrapure water, is made possible.

The detector probe, or cell can be packaged in a volume as small as 1 cubic centimeter. When used as a probe for an ion detector, the housing then is in the form of a flowthrough tube, permitting the test water or electrolyte to flow into and surround the electrodes 11 and 12. There is no time delay in obtaining the reading, because as soon as the electrolyte surrounds the electrodes, the reading is immediately obtained.

Figure 2:
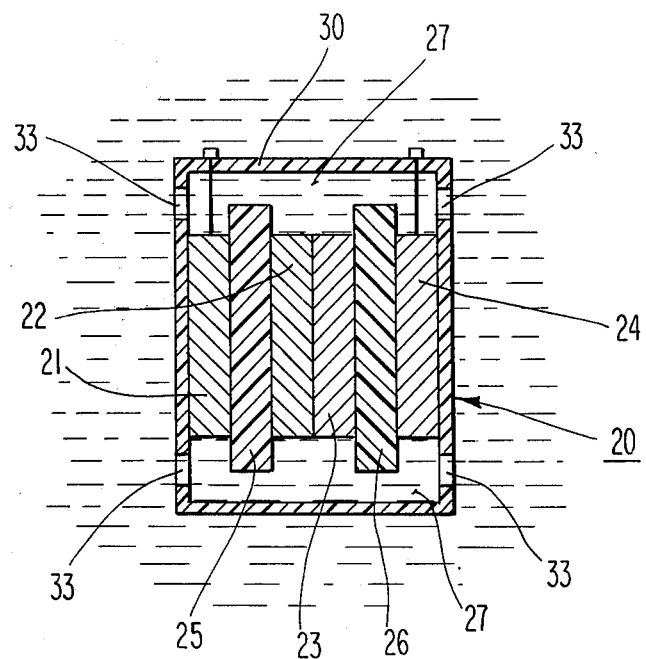
FIG. 2 is a schematic diagram of another embodiment of the ion generating cell of this invention incorporating additional elements to modify the internal impedance characteristic of the cell.

Referring now to FIG. 2, there is shown a schematic diagram of another embodiment of this invention, which embodiment provides a cell with means for lowering the internal impedance thereof. The cell 20 comprises a housing 30, suitably made of polyvinylchloride or another like material, which housing may have openings 33 for permitting flow of an electrolyte into the inner chamber 27. It is to be noted that the housing 30 may be solid, in which case it encloses an electrolyte which is placed in inner chamber 27. For the application where it is desired to use the cell as a probe, so as to test an electrolyte, or where it is desired to provide electrolyte flow-through for any other reason, the openings 33 will be included.

A first electrode 21 is shown, which preferably is made of copper which has been irradiated in the same way as the copper electrode of FIG. 1. This electrode may suitably be made of sponge copper, is suitably 2 inches square and 0.25 inch in thickness. Positioned next to it is a plastic element 25, suitably polyurethane or any like plastic capable of acting as an ion transport medium. Element 25 may have a thickness of about 0.25 inch but also an area slightly larger than electrode 21. Proceeding from left to right, to the right of polyurethane element 25 is an element 22 of another metal, suitably zinc, which in this illustration is typically about 0.015 inch in thickness. Positioned right next to and in contact with element 22 is another element 23 which suitably comprises irradiated sponge copper, being approximately 0.25 inch in thickness. To the right of element 23 is a second plastic or polyurethane element 26, of the same approximate size as element 25. Finally, to the right of plastic element 26, is another electrode 24, which suitably may be aluminum, having a thickness of about 0.015 inch. Elements 21, 25, 22, 23, 26 and 24 are, in the preferred embodiment, positioned tightly against each other. Output leads and connect through the housing to output terminals and providing output means from which to take the electrical output of the cell.

The construction of the embodiment shown in FIG. 2 provides for a cell, or generating device having a lowered internal impedance. The polyurethane members 25 and 26 are in snug contact with adjacent members, and provide very effective ion transport members for transport thereacross of ions from the electrolyte. In practice, it has been found that the thickness of the polyurethane is of no practical effect, and while an illustrative thickness of 0.25 inch has been given, such thickness could be made many times greater without affecting the output characteristic. The inclusion of the transport members provides a rather low impedance cell which is very useful for powering low impedance loads. This cell, when immersed in 0.005 mho/cm water, has an internal impedance of about 40 ohms, and when driving a load of about 40 ohms provides about 30 $\mu$a at about 1.2 volts. It is to be noted that, if the copper elements 21 and 23 are not irradiated, the output voltage drops to about 0.7 volts.

The illustrations presented in the specification disclose embodiments of a novel device, and a method of making same, which provides a predictable output current for a given ion concentration of electrolyte. When used as an ion detector, the cell is extremely accurate and reliable in providing a signal representative of ion concentrations in trace amounts, and in particular amounts around 1 PPM and less. It is to be noted that the reliability of the device, when used as an ion detector, comes from the fact that the signal being generated is derived directly from the ion concentration. This is in contradistinction to the prior art method whereby an external source is utilized to pass a current through an ion concentration, in which case a conductivity measurement is taken to derive an indication of ion concentration. All of the difficulties attendant conductivity measurements are eliminated in the device and method of this invention. When used as a simple cell, the internal impedance can be varied by varying the ion concentration of the electrolyte and by building transport means into the cell between the output electrodes. By designing the internal impedance, matching of the power cell to the expected load may be achieved, to further maximize power output. The cell, in either of the illustrated embodiments, in a rugged solid state device which is adaptable for a wide variety of uses. It has many advantages over the prior art, including the facts that it can be made very small and it is not vulnerable to diminished life when on the shelf.

We claim:

1. A generating device comprising:
   a. a housing containing electrolyte;
   b. a first electrode having a first predetermined surface area immersed in said electrolyte within said housing, said first electrode being of a first metallic composition and having been irradiated with electromagnetic energy in a range centered around about 1.378 A;
   c. a second electrode having a second predetermined surface area immersed in said electrolyte within said housing, said second electrode being of a second metallic composition; and
   d. output means connected to said electrodes for providing an electrical output on the outside of said housing.

2. The generating device of claim 1, wherein said housing is closed and said electrolyte is contained therein.

3. The generating device as described in claim 1, wherein said housing has openings adapted to permit electrolyte to flow through said housing.

4. The generating device as described in claim 3, wherein said first electrode is irradiated copper.

5. The generating device as described in claim 2, wherein said first electrode is irradiated copper.

6. The generating device as described in claim 1, wherein said first electrode comprises copper that has been irradiated by electromagnetic energy in the range of $10^4$ to $10^7$ eV.

7. The generating device as described in claim 6, wherein said energy is in the vicinity of 8950 eV.

8. The generating device as described in claim 1, wherein the composition of said second electrode comprises at least one element selected from the group consisting of the elements of the periodic groups I, II, VI, VII and VIII of the Periodic Table.

9. The generating device of claim 8, wherein said second electrode composition comprises at least two metals selected from the group consisting of elements in groups I, II and VIII of the Periodic Table.

10. The generating device of claim 1, wherein said first electrode comprises copper that has been irradiated with radiation suitable to excite K shell electrons of said copper.

11. The generating device of claim 1, in combination with current reading means connected to said output means for reading the current produced by said device, said current being representative of the ion concentration in said electrolyte for a range of ion concentrations.

12. The generating device of claim 1, comprising inner means positioned between said first and second electrodes for adjusting the internal impedance of said device.

13. The generating device of claim 12, wherein said inner means comprises polyurethane.

14. A generating device, comprising:
 a. a housing containing electrolyte;
 b. a first electrode of a first metallic composition comprising irradiated copper which has been irradiated with high frequency electromagnetic radiation;
 c. a second metallic electrode, having a second metallic composition;
 d. ion transport means having a plastic composition for providing an ion transport path between said first and second electrodes;
 e. said electrodes and ion transport means being positioned so that they are immersed in said electrolyte; and
 f. output means for connecting said electrodes to respective terminals on the outside of said housing.

15. The generating device as described in claim 14, wherein said second electrode comprises aluminum.

16. The generating device as described in claim 15, wherein said ion transport means comprises polyurethane.

17. The generating device as described in claim 16, wherein said housing contains flow-through openings.

18. The generating device as described in claim 14 wherein said ion transport means is a first plastic element, and comprising
 a. a second plastic element;
 b. an irradiated copper element which has been radiated with high frequency electromagnetic radiation; and
 c. an element of a third metallic composition, said irradiated copper element and third element being sandwiched between said first and second plastic elements, with said first and second electrodes positioned outside of said first and second plastic elements respectively.

19. The generating device as described in claim 18, wherein said first electrode and said copper element are made of sponge copper, said second electrode is made of aluminum, said plastic elements are made of polyurethane, and said third element comprises zinc.

20. The generating device as described in claim 18, wherein said plastic elements have a surface area in excess of that of said electrodes and the other elements.

21. A method of making a device adapted to generate a current, comprising:
 a. irradiating a copper electrode with electromagnetic radiation having a frequency spectrum including wavelengths around 1.378 A;
 b. combining said irradiated copper electrode with an electrode of a dissimilar metallic composition, and connecting output terminals to said electrodes; and
 c. immersing said electrodes in an electrolyte.

22. The method as described in claim 22, wherein the electrolyte contains an ion concentration which is to be measured, and comprising the further steps of measuring current flow from said output terminals and obtaining from said measured current flow a reading of ion concentration.

23. A device adapted to produce an electrical output when combined with an electrolyte, comprising:
 a. a housing adapted to contain electrolyte;
 b. a first electrode of a first metallic composition comprising irradiated copper which has been irradiated with high frequency electromagnetic radiation, mounted within said housing;
 c. a second electrode of a second metallic composition, mounted within said housing; and
 d. output means connected to said electrodes for providing an electrical output.

* * * * *

UNITED STATES PATENT AND TRADEMARK OFFICE
CERTIFICATE OF CORRECTION

PATENT NO. : 4,074,027

DATED : February 14, 1978

INVENTOR(S) : Raymond F. Akers and Frank Malley

It is certified that error appears in the above–identified patent and that said Letters Patent are hereby corrected as shown below:

Column 5, line 34, delete "and"
Column 5, line 35, delete "and"

Signed and Sealed this

Sixth Day of June 1978

[SEAL]

Attest:

RUTH C. MASON
*Attesting Officer*

DONALD W. BANNER
*Commissioner of Patents and Trademarks*